United States Patent [19]
Leighton et al.

[11] Patent Number: 5,690,311
[45] Date of Patent: Nov. 25, 1997

[54] FLOOR CLAMP FOR AN ANALYZER

[75] Inventors: Roger Gaylord Leighton, Rochester; Michael Erwein Bausch, Livonia, both of N.Y.

[73] Assignee: Johnson & Johnson Clinical Diagnostic, Rochester, N.Y.

[21] Appl. No.: 626,552

[22] Filed: Apr. 2, 1996

[51] Int. Cl.⁶ ............................................. F16M 7/00
[52] U.S. Cl. ...................... 248/681; 248/500; 292/209; 292/DIG. 49
[58] Field of Search ....................... 248/500, 506, 248/680, 681, 154, 349.03, 221.11, 222.51, 222.52, 682; 292/209, 223, DIG. 49

[56] References Cited

U.S. PATENT DOCUMENTS

| | | | |
|---|---|---|---|
| 989,085 | 4/1911 | Turton | 248/680 |
| 1,063,716 | 6/1913 | McLaughlin | 248/681 |
| 1,064,005 | 6/1913 | Pritzl . | |
| 1,064,712 | 6/1913 | Corcoran | 248/681 |
| 2,256,447 | 9/1941 | Burke | 292/223 |
| 2,371,896 | 3/1945 | Knauer . | |
| 2,893,773 | 7/1959 | Clifton, Jr. | 292/223 |
| 3,045,465 | 7/1962 | Larson | 292/223 X |
| 5,176,437 | 1/1993 | Remington | 248/680 X |

FOREIGN PATENT DOCUMENTS

26 08 333   9/1977   Germany ................ 248/681

Primary Examiner—Alvin C. Chin-Shue
Assistant Examiner—Derek J. Berger
Attorney, Agent, or Firm—Dana M. Schmidt

[57] ABSTRACT

A clamp for holding an analyzer in place on a horizontal surface, comprising an entrance mouth angled to allow insertion of a bracket of the analyzer without initial accurate alignment, and a tongue-and-opening interlock between the clamp and the bracket on the analyzer, sized to give limited sideways movement between the clamp and analyzer, once the clamp is locked onto the bracket. The clamp is locked to the bracket using a spring effective to adjust for dimensional variations.

8 Claims, 7 Drawing Sheets

FLOOR CLAMP FOR AN ANALYZER

FIELD OF THE INVENTION

This invention relates to a clamp for holding a mainframe apparatus to a surface such as a floor.

BACKGROUND OF THE INVENTION

Clamps for holding articles to a horizontal surface are known. For example, U.S. Pat. No. 1,064,005 discloses a clamp comprising a frame 4 having a fixed portion projecting upwardly away from surface 3 to receive below that portion a bracket or screw 6 secured to the apparatus being clamped. A locking lever 7 is pivotally mounted by biasing spring 10 to pivot about axle 7a bimodally between an open, receiving position, FIG. 5, to a locked position, FIG. 4, in which it engages bracket or screw 6 below the top of the upwardly projecting portion of clamp frame 4. However, a drawback to such a clamp is that the mouth of frame 4 that receives screw 6 for locking, is a cylindrical portion that projects exactly vertically, leaving no entrance to the mouth larger than the locking portion. As a result, screw 6 has to be accurately aligned with the opening in order for it to enter. This requires visual alignment before attempting to insert screw 6. Although that may be adequate for a desk clamp for a typewriter (the '005 patent), it is not adequate for a floor clamp for a mainframe analyzer. The bulk of such an analyzer precludes visual alignment during clamping.

Still further, once screw 6 is inside frame 4 in the clamp of the '005 patent, there is only clamp lever 7 that engages it. That lever is not adequate to keep the screw from sideways slippage within frame 4, and no other interconnect is provided between the screw and the frame. Such sideways slippage may not be a problem when holding down a typewriter, but it is a problem for clamping down mainframe analyzers. Particularly that is true when the analyzer is used in an automated laboratory, by rolling it up to a continuous track on which sample tubes are processed robotically. In such a case, precision positioning is important.

Accordingly, prior to this invention there has been a need for a floor clamp that, with a minimum of effort by the operator, will readily hold a mainframe analyzer on a floor in a precise location.

SUMMARY OF THE INVENTION

We have designed a floor clamp that solves the above-noted problems.

More specifically, there is provided a clamp for holding an analyzer in place on a horizontal surface, comprising: a frame bolted to the surface with a portion thereof fixed a predetermined distance away from the surface to accommodate a mounting bracket on the analyzer so that some of the bracket is locatable in contact with the frame and between the fixed portion and the surface; an axle mounted on the frame; a locking jaw pivotally mounted on the axle; an actuator mounted to force the jaw to pivot from an open position effective to receive the mounting bracket, to a locking position effective to lock the bracket against the fixed portion of the frame; the fixed portion of the frame further comprising shoulder means defining a mouth extending from an entrance into the frame towards the portion fixed above the horizontal surface, the shoulder means being effective to guide the mounting bracket to the fixed portion of the frame, the shoulder means being angled from the fixed portion outwardly away therefrom towards the entrance at an angle such that the mouth is larger at the entrance than at the fixed portion, so that the mounting bracket can enter the mouth without being precisely aligned; and a tongue-and-opening interlock between the frame and the bracket, the tongue being an integral projection from one of the frame portion and the bracket, and the opening being formed in the other of the frame portion and the bracket, the opening being sized to provide sideways constraint against sideways movement of the bracket within the mouth.

Accordingly, it is an advantageous feature of the invention that a floor clamp is provided which guides the analyzer into a locking engagement with a minimum of visual inspection by the operator, and at the same time minimizes sideways slippage once clamped.

Other advantageous features will become apparent upon reference to the following Detailed Description when read in light of the attached drawings.

DESCRIPTION OF THE PREFERRED EMBODIMENTS

The invention is hereinafter described in connection with certain preferred embodiments, in which the analyzer being clamped is an analyzer described in U.S. Pat. No. 5,008,082, the clamp comprises upper and lower frame portions tongue-and-grooved together, and the clamp lever is of a particular shape. In addition, the invention is applicable regardless of the kind of analyzer clamped in place, regardless of how the clamp frame portions are assembled, and regardless of the shape of the clamp lever.

Figure 1:
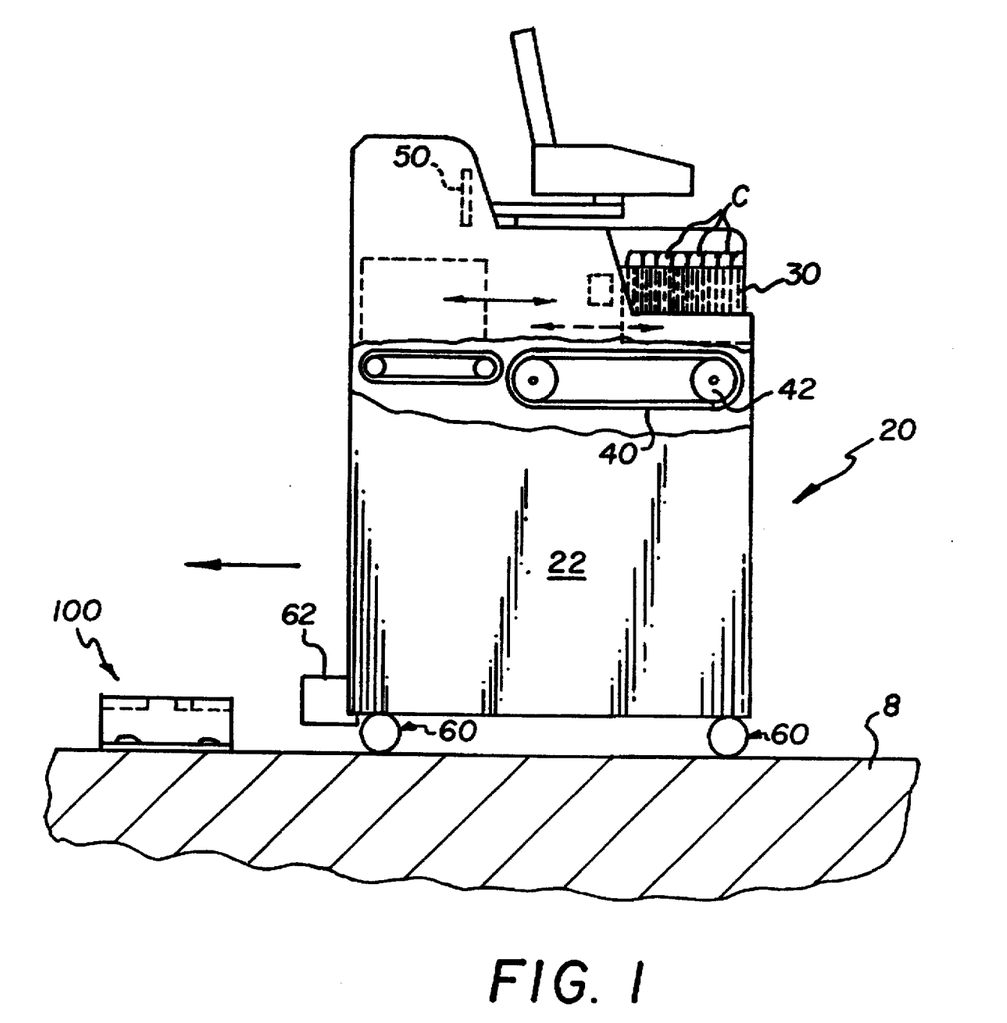
FIG. 1 is a side elevational view of an analyzer moving into clamping engagement with a clamp constructed in accordance with the invention.

As noted, the clamp of this invention is intended, FIG. 1, to clamp to the floor 8 of a building, a clinical analyzer 20 comprising a frame 22, a sample supply station 30, means 40 for carrying sample containers C into the analyzer, an aspirator 50 for removing sample from containers C, and a test station for depositing sample onto or into a suitable testing medium, not shown, for detection at a detection station, also not shown. As shown, analyzer 20 is preferably that described in the aforesaid '082 patent. It is mounted on casters 60, and carries a bracket 62 for engaging clamp 100 of the invention.

Figure 2:
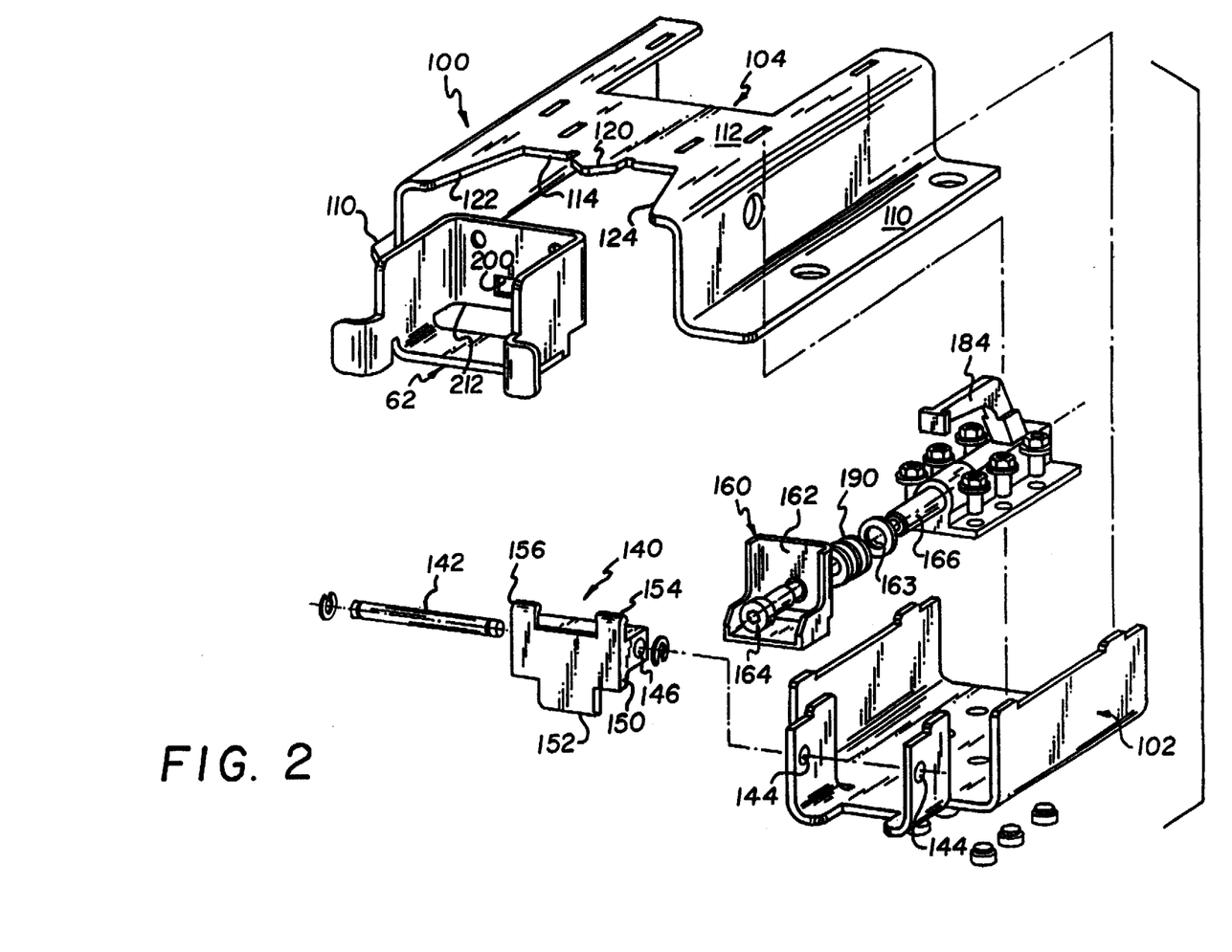
FIG. 2 is an exploded isometric view of the clamp of FIG. 1.
Figure 4:
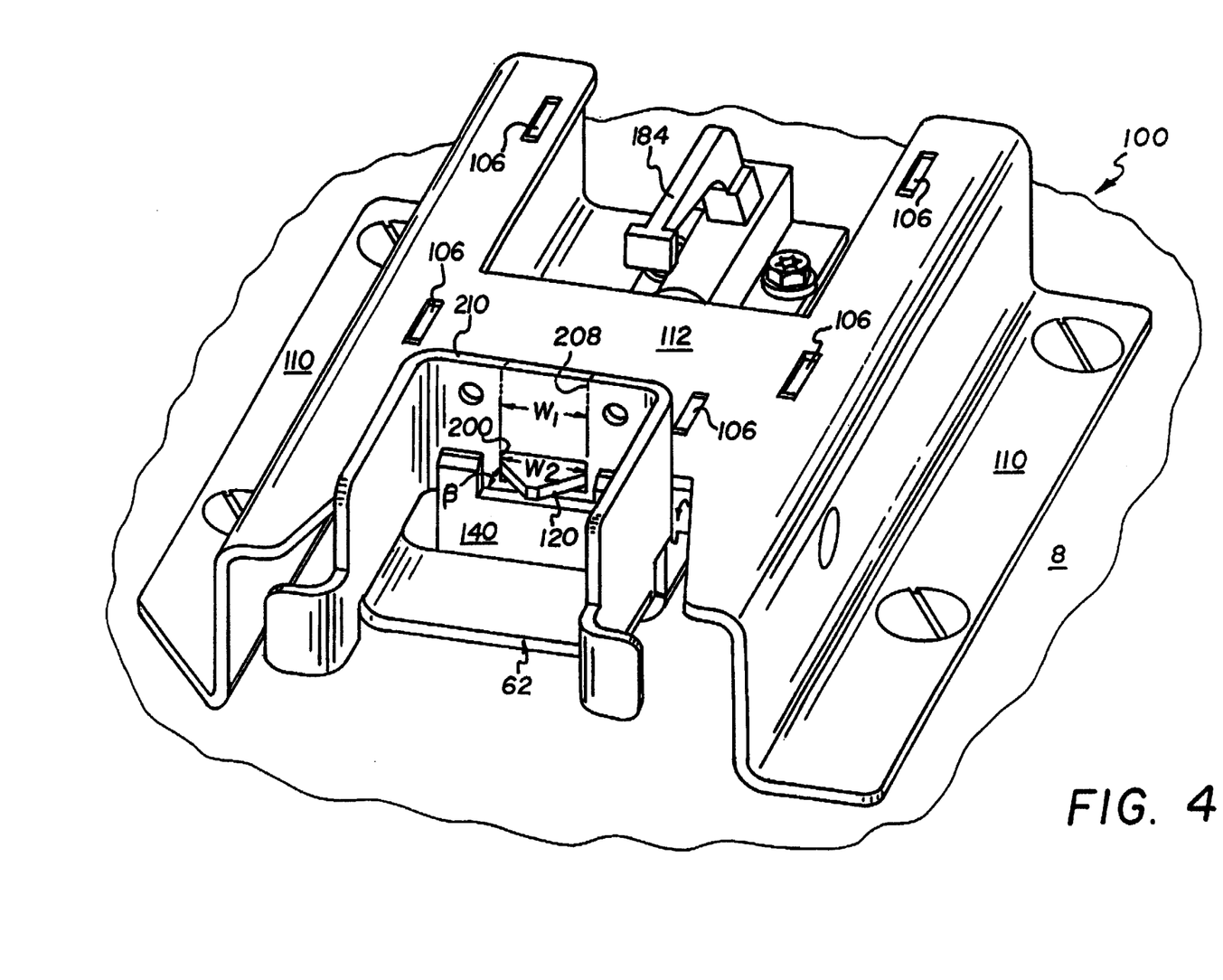
FIG. 4 is an isometric view of the analyzer bracket (without the analyzer) clamped to the clamp of the invention.

In accordance with the invention, clamp 100 comprises, FIG. 2, a frame preferably provided in two parts—lower frame member 102 and upper frame member 104 welded into engagement with each other, such as by tongue-and-slot connections welded at various places 106, as shown in FIG. 4. Upper frame member 104 preferably includes side flanges 110 boltable to floor 8. A portion 112 extends, between the side flanges, raised and fixed a predetermined vertical distance above the surface of floor 8. When viewed in plan, portion 112 is preferably H-shaped, and includes a contact edge 114 and a tongue 120 projecting outwardly from edge 114.

Edge 114 in turn is bordered by guide shoulders 122 and 124 which extended outwardly from edge 114. The shoulders also extend sideways at an angle alpha away from the normal (130) extending from a position adjacent the intersection of edge 114 and either shoulder, FIG. 5. The effect is to create an entrance mouth "E" which allows for a deviation of 2α for an incoming bracket 62, described further below, away from perfect alignment with normals 130. That is, the larger opening of mouth E, compared to contact edge 114, renders alignment using guide shoulders 122,124, easy, even in the absence of visual inspection.

A jaw 140 is pivotally mounted to the lower frame member 102, on pivot pin 142 journaled to member 102 at apertures 144, FIG. 2. Pin 142 passes through jaw 140 via aperture 146, located in back of the center of gravity, that is, to the right of the center of gravity 150 of the jaw as shown in FIG. 2, sufficiently to cause jaw 140 to swing to its open position, FIG. 3A, if left alone.

Jaw 140 further includes a camming lip 152 pendent therefrom and generally centered on the jaw, and gripping fingers 154, 156 on the outer edges of the jaw and rising from the jaw generally opposite to the lip 152.

Figure 3A:
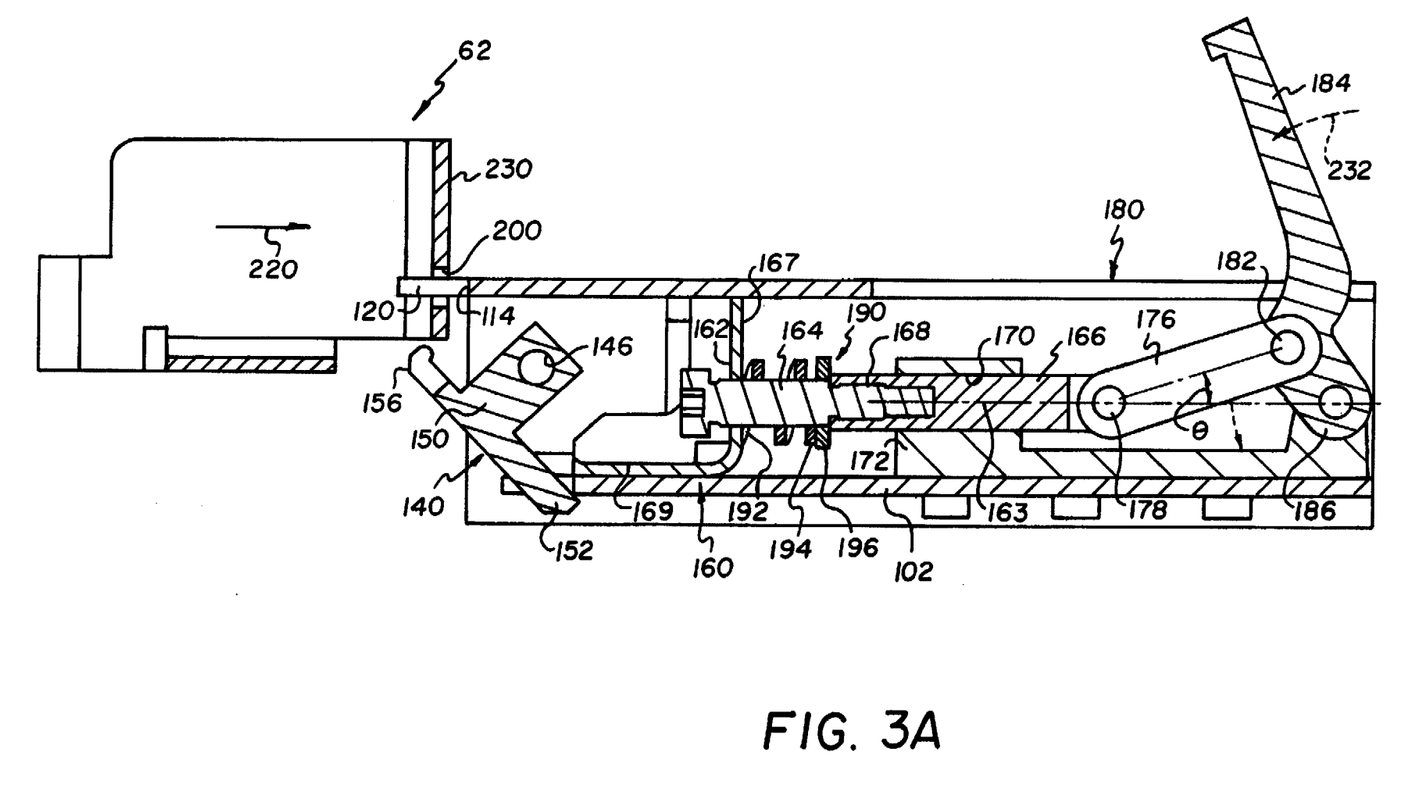
FIGS. 3A and 3B are elevational views in section taken generally through the axis 163 of the rod shown in FIG. 2, depicting in FIG. 3A the "open" position and in FIG. 3B the "closed" or "locked" position.
Figure 3B:
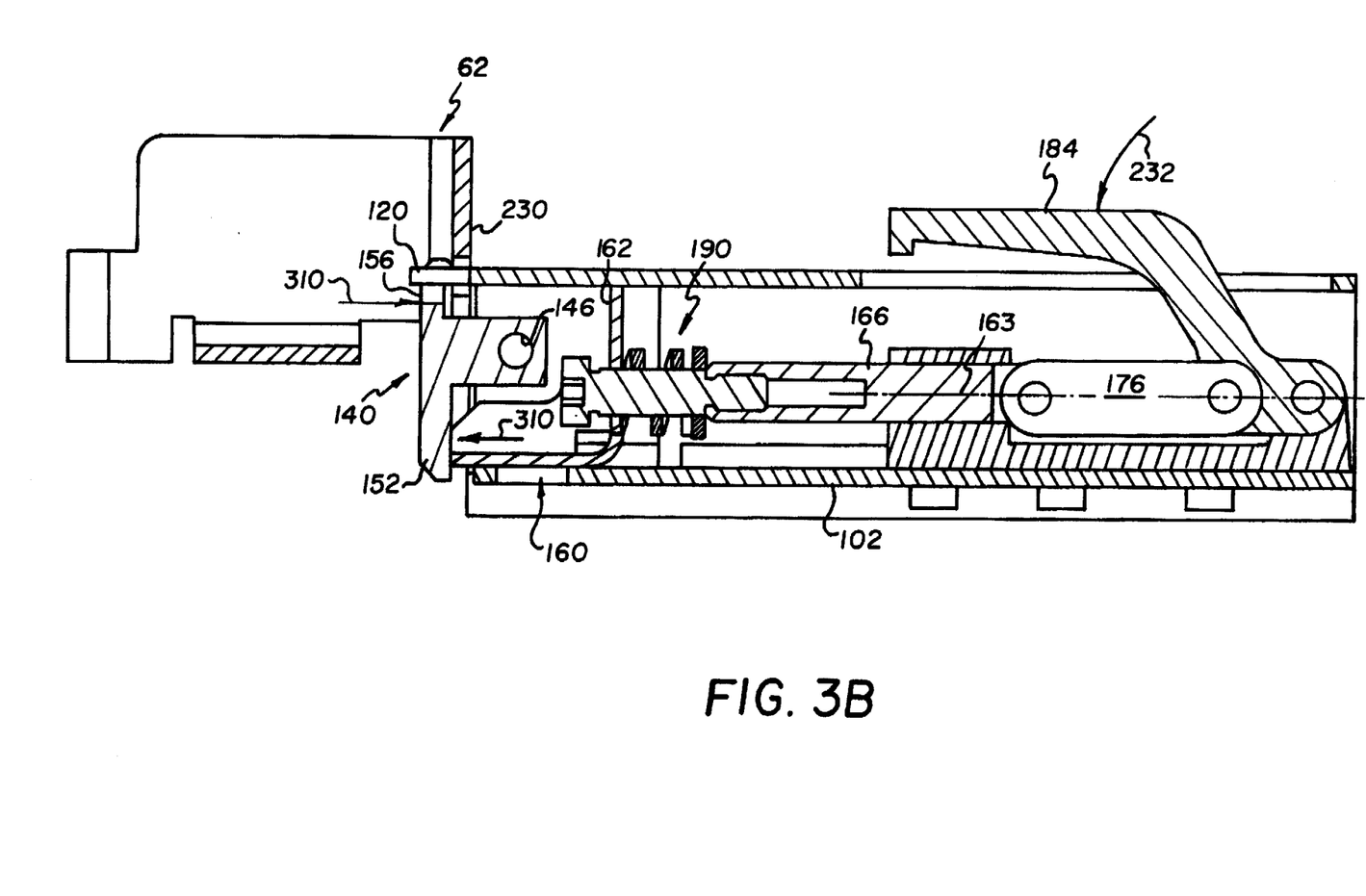

To force jaw 140 to move bimodally between its open position, FIG. 3A, and its closed, gripping position, FIG. 3B, an actuator 160 is provided, FIG. 2. Most preferably, actuator 160 comprises a plate 162, preferably shaped as a "J", loosely mounted on a rod having a center axis 163 and comprising a keeper bolt 164 and a push-pull plunger 166. See especially FIGS. 3A and 3B. Plate 162 comprises a vertical portion 167 and a horizontal leg 169.

Bolt 164 is screwed into a first end 168 of plunger 166. Plunger 166 reciprocates through opening 170 in boss 172 that is bolted to lower frame member 102, FIG. 2.

To lock jaw 140 closed and actuator 160 in place against the closed jaw, means 180 are provided, FIG. 3A, in the form of a connecting link 176 one end 178 of which is pivotally connected to plunger 166, and the other of which is pivotally connected at 182 to an over-the-center manual handle 184 pivoted at an end 186 to boss 172 with connection 182 being closer to plunger 166 than is end 186.

The resulting over-the-center toggle connection of handle 184 to actuator 160 produces a locking force $T_F$, arrows 310 of FIG. 3B, of the actuator against jaw 140 and the jaw against bracket 62, that is equal to F cos ∅, where F is the instantaneous downward component of the force delivered, arrow 232, on handle 184, and ∅ is the instantaneous angle noted in FIG. 3A, between arm 176 and the axis of plunger 166 (denoted as "330").

To allow for dimensional variations in all the parts, such as in the thickness of bracket 62, an compression spring 190 is disposed between actuator plate 162 and means 180. More specifically, end 192 of spring 190 presses plate 162 to the left, FIG. 3A, and opposite end 194 of spring 190 presses a washer 196 on plunger 166 to the right. The spring, being compressible, will allow for dimensional variations as jaw 140 closes onto a bracket 62, FIG. 3B. However, because of the large mass attached to bracket 62 (shown in FIG. 1), spring 190, FIG. 2, is preferably itself massive enough to accommodate the inertial forces that analyzer 20 tends to deliver. Thus, spring 190 should have a final spring force of at least about 125 pounds for use with a mainframe analyzer such as analyzer 20.

To cooperate with tongue 120, an opening such as slot 200 is formed in bracket 62, at the height where bracket 62 will intersect tongue 120. Most preferably, FIG. 4, slot 200 is formed with a size and especially an inside width "$W_1$", that closely fits against outside width $W_2$ of tongue 120, thus providing close sideways constraint against sideways movement of bracket 62 within the mouth formed by shoulders 122,124. Most preferably, there is only about 0.06 cm difference between $W_1$ and $W_2$.

To allow such a tight-fitting relationship to come to a closure, tongue 120 is provided with camming surfaces 202 and 204 sloped inwardly, giving tongue 120 an arrow-shape. By being inwardly sloped at an angle beta, each surface 202 and 204 acts to cam slot 200 into centered engagement around tongue 120, if bracket 62 is at first mis-aligned with tongue 120.

Alternatively, slot 200 can be formed as a groove 208 (in phantom) extending down from top edge 210 of bracket 62, or up (not shown) from bottom edge 212 of bracket 62 (FIG. 2), instead of as a closed slot.

Figure 5:
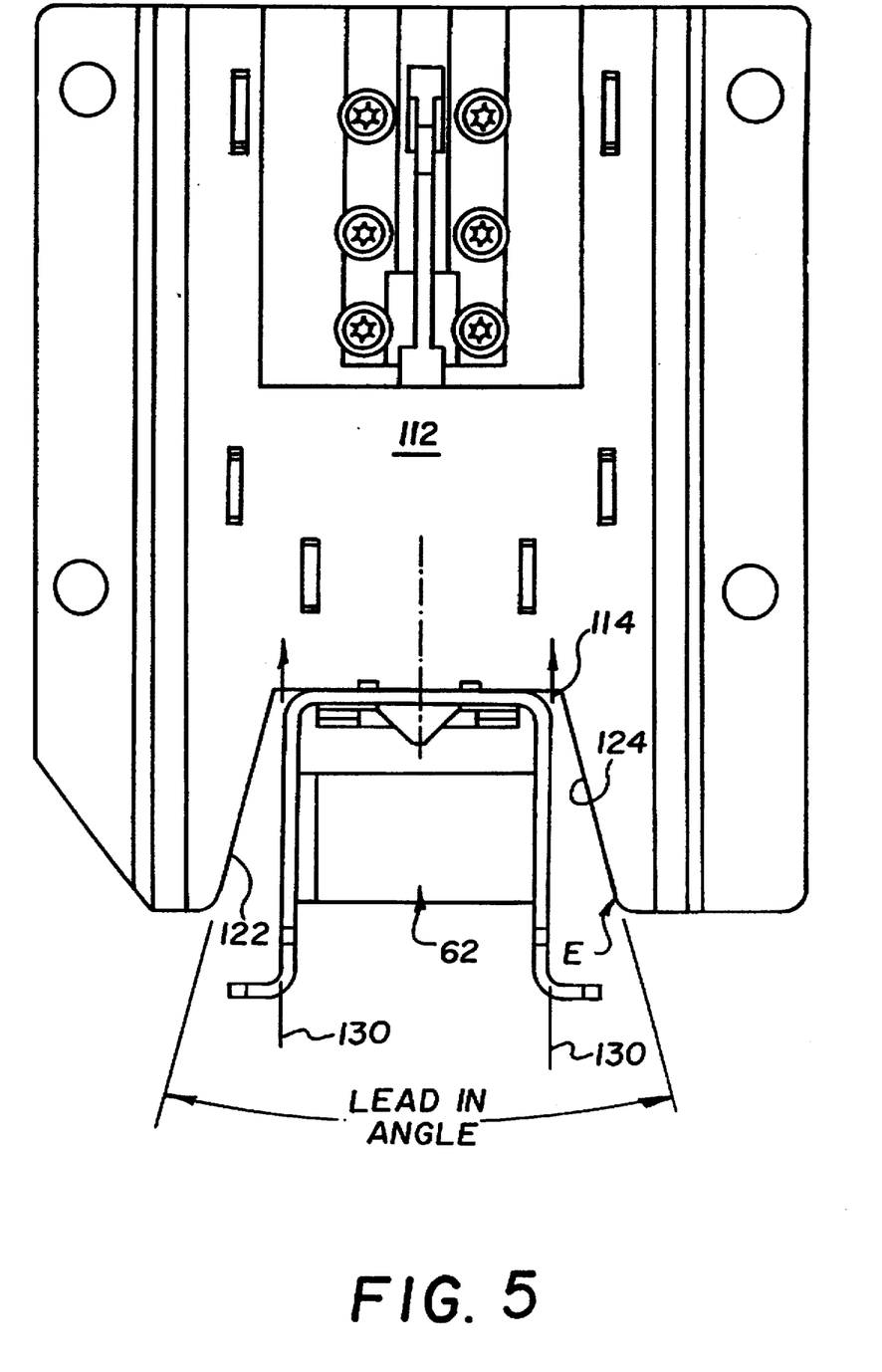
FIG. 5 is a top plan view of the clamped arrangement of FIG. 2.

As a result, substantial sideways motion is tolerated as bracket 62 is pushed into the mouth of shoulders 122,124, FIG. 5, and towards tongue 120. However, as slot 200 slides over the tongue, the tight tolerances between $W_1$ and $W_2$, FIG. 4, ensure that, once locked by jaw 140, no sideways motion can occur between bracket 62 and clamp 100.

In use, handle 184 is first raised, FIG. 3A, so that plunger 166 and plate 162 are withdrawn (to the right as shown). This allows jaw 140 to fall by gravity into its "open" position, in which bracket 62 can be pushed, arrow 220, so that slot 200 slides over tongue 120. When exterior face 230 of bracket 62 contacts edge 114 of clamp 100, handle 184 is pushed manually downward, arrow 232, pushing arm 176 downward and forcing plunger 166 to move to the left. Spring 190 then pushes actuator 160 and specifically leg 169 against lip 152 of jaw 140, forcing it, FIG. 3B, to pivot to its locked position with fingers 154,156 clamped tightly against bracket 62 (attached to analyzer 20). Spring 190 compresses only to the extent necessary to accommodate tolerance changes in the connections. Release of the clamping action occurs by the reverse operation, as will be apparent.

Figure 6:
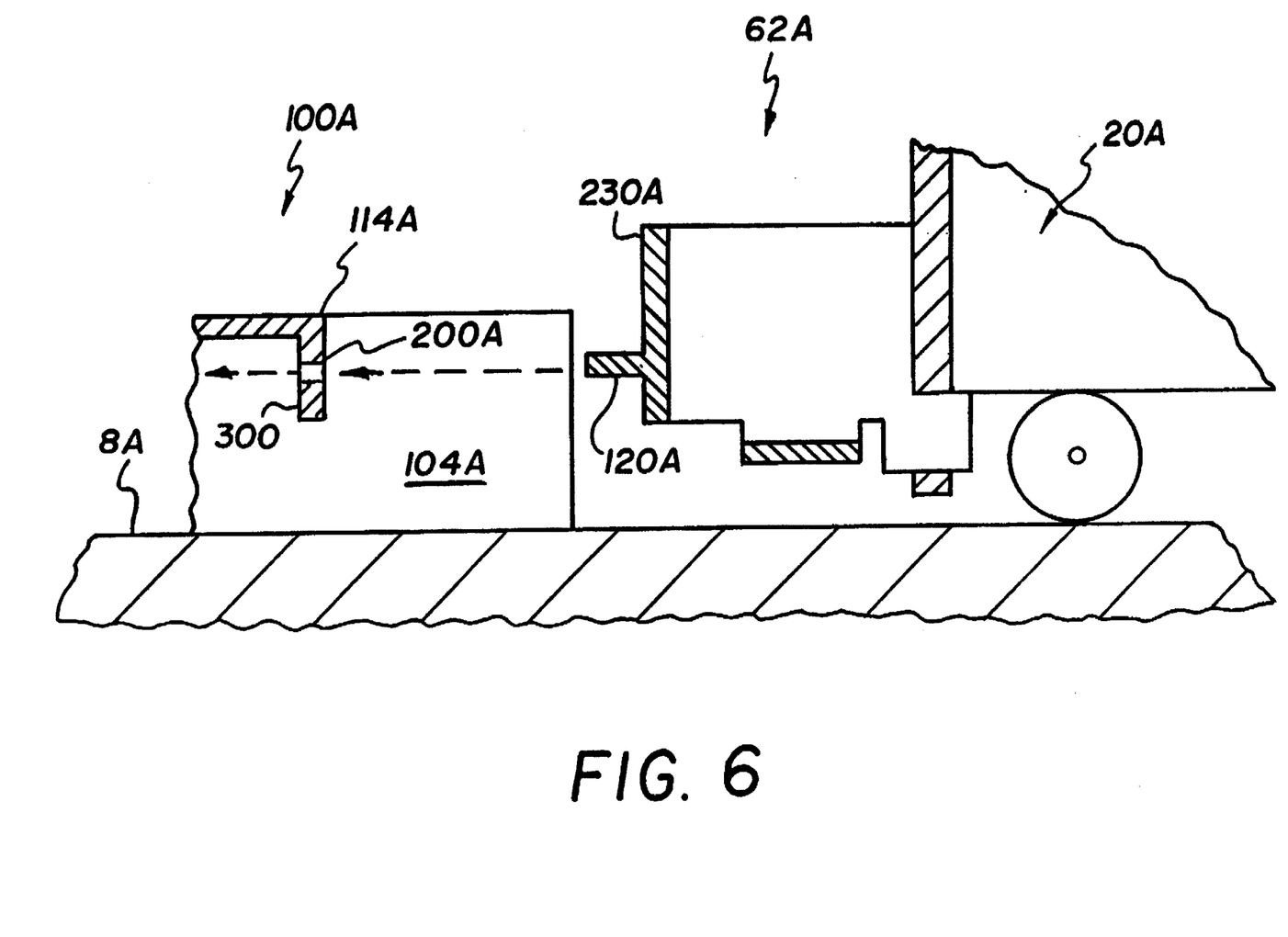
FIG. 6 is a fragmentary side elevational view in section of an alternate embodiment of the invention, with the clamp handle, link, and actuator removed for clarity.

Alternatively, FIG. 6, the tongue and opening interlock between the bracket and the clamp can be reversed. Parts similar to those previously described bear the same reference numeral, to which the distinguishing suffix "A" is appended. Thus, analyzer 20A is bolted to or otherwise integral with bracket 62A, and clamp 100A is bolted to floor 8A, as described above. Indeed, all parts are the same as previously described, except that tongue 120A extends outwardly from exterior surface 230A of bracket 62A, rather than the clamp. Opening 200A is now a slot in a lip 300 depending from edge 114A of upper frame member 104A, rather than in the bracket.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In combination, a mounting bracket on an analyzer, and a clamp for holding said analyzer in place on a horizontal surface, said claim comprising:
   a frame capable of being bolted to said surface with a portion thereof fixed a predetermined distance away from said surface to accommodate said mounting bracket so that some of said bracket is locatable in contact with said frame and between said fixed portion and said surface;

an axle mounted on said frame;

a locking jaw pivotally mounted on said axle;

an actuator mounted to force said jaw to pivot from an open position effective to receive said mounting bracket, to a locking position effective to lock said bracket against said fixed portion of said frame;

said fixed portion of said frame further comprising shoulder means defining a mouth extending from an entrance into said frame towards said portion fixed above said horizontal surface, said shoulder means being effective to guide said mounting bracket to said fixed portion of said frame, said shoulder means being angled from said fixed portion outwardly away therefrom towards said entrance at an angle such that said mouth is larger at said entrance than at said fixed portion, so that said mounting bracket can enter said mouth without being precisely aligned; and a tongue-and-opening interlock between said frame and said bracket, said tongue being an integral projection from one of said frame portion and said bracket, and said opening being formed in the other of said frame portion and said bracket, said opening being sized to provide sideways constraint against sideways movement of said bracket within said mouth.

2. A combination as defined in claim 1, and further including lock means for locking said actuator in place against said jaw when said jaw is in said locking position.

3. A combination as defined in claim 2, and further including a spring disposed between said lock means and said actuator.

4. A combination as defined in claim 2, wherein said lock means includes a handle, and an over-the-center toggle connection of said handle to said actuator.

5. A combination as defined in claim 1, wherein said tongue is part of said frame portion and said opening is disposed within a portion of said bracket.

6. A combination as defined in claim 1, wherein said tongue is part of said bracket and said opening is disposed within a portion of said frame.

7. A combination as defined in claim 1, and further including a floor of a building comprising said surface.

8. A combination as defined in claim 1, wherein said jaw has a center of gravity that is positioned relative to said axis such that said jaw pivots downwardly when not forced to said locking position by said actuator.

* * * * *